(12) United States Patent
Yoshimura

(10) Patent No.: US 10,698,425 B2
(45) Date of Patent: Jun. 30, 2020

(54) FLUID ANALYSIS APPARATUS AND FLUID ANALYSIS METHOD

(71) Applicant: HORIBA, Ltd., Kyoto (JP)

(72) Inventor: Tomoshi Yoshimura, Kyoto (JP)

(73) Assignee: HORIBA, LTD., Kyoto (JP)

( * ) Notice: Subject to any disclaimer, the term of this patent is extended or adjusted under 35 U.S.C. 154(b) by 214 days.

(21) Appl. No.: 15/817,374

(22) Filed: Nov. 20, 2017

(65) Prior Publication Data

US 2018/0164838 A1 Jun. 14, 2018

(30) Foreign Application Priority Data

Dec. 9, 2016 (JP) .................................. 2016-239423

(51) Int. Cl.
*G01M 15/10* (2006.01)
*G05D 7/06* (2006.01)
*G01N 33/00* (2006.01)
*G01N 1/22* (2006.01)

(52) U.S. Cl.
CPC ........ *G05D 7/0652* (2013.01); *G01M 15/102* (2013.01); *G01N 1/2252* (2013.01); *G01N 33/0009* (2013.01); *G01N 33/0037* (2013.01)

(58) Field of Classification Search
CPC . G05D 7/0652; G01M 15/102; G01N 1/2252; G01N 33/0009; G01N 33/0037
See application file for complete search history.

(56) References Cited

U.S. PATENT DOCUMENTS

| 9,500,144 B1 * | 11/2016 | Steen ..................... F02M 25/00 |
| 2012/0266687 A1 | 10/2012 | Takahashi |
| 2016/0139013 A1 * | 5/2016 | Gorbunov ............ G01N 1/2247 |
| | | 73/28.01 |

FOREIGN PATENT DOCUMENTS

| JP | 08005557 A | 1/1996 |
| JP | 11-064339 A | 3/1999 |
| WO | 2014202771 A2 | 12/2014 |

OTHER PUBLICATIONS

EESR dated Feb. 23, 2018 issued for European Patent Application No. 17 203 888.7.

* cited by examiner

Primary Examiner — P. Macade Nichols
(74) Attorney, Agent, or Firm — Brooks Kushman P.C.

(57) ABSTRACT

The present invention intends to reduce the contamination level of an introduction path, miniaturize a circuit board, and improve measurement accuracy by adjusting the number of molecules of a measurement target component to flow into an analysis part, and includes: a detector for detecting the concentration of the measurement target component contained in fluid; an introduction path connected to the detector to introduce the fluid into the detector; and a flow rate switching mechanism adapted to, depending on the concentration of the measurement target component, switch the flow rate of the fluid to be introduced into the detector.

10 Claims, 6 Drawing Sheets

FLUID ANALYSIS APPARATUS AND FLUID ANALYSIS METHOD

CROSS-REFERENCE TO RELATED APPLICATION

This application claims priority to JP Application No. 2016-239423, filed Dec. 9, 2016, the disclosure of which is incorporated in its entirety by reference herein.

TECHNICAL FIELD

The present invention relates to a fluid analysis apparatus and a fluid analysis method adapted to analyze the concentration of a component contained in exhaust gas discharged from, for example, an internal combustion engine.

BACKGROUND ART

As apparatuses adapted to analyze the concentrations of hydrocarbon (HC) and nitrogen oxide (NOx) contained in exhaust gas discharged from, for example, an internal combustion engine, there are ones using a hydrogen flame ionization analysis method (FID) and a chemiluminescence analysis method (CLD), respectively.

When a required range for measuring the concentration of a measurement target component is wide, such as in the case of FID or CLD, to deal with such a situation, the amplification factor of an amplifier for amplifying an analog signal outputted from a detector is switched. For example, when the concentration of a measurement target component is high, a small amplification factor is used, whereas when the concentration is low, a large amplification factor is used. In addition, when measuring a measurement target component of high concentration, the linearity between the analog signal outputted from the detector and the concentration tends to be lost, and therefore it is necessary to use a high order calibration curve coefficient.

When measuring a measurement target component of high concentration, the above-described measures may be taken; however, the following problems exist.

That is, a large amount of the measurement target component (molecules) flows into the detector, and consequently, an introduction path to the detector may be contaminated to increase a background level. Also, the amplifier is required to have multiple amplification factors, causing one of adverse effects on miniaturization of a circuit board. Further, as the concentration of the measurement target component increases, the linearity between the analog signal outputted from the detector and the concentration is lost, and therefore it is necessary to ensure the linearity by employing a high order calibration curve coefficient.

CITATION LIST

Patent Literature

Patent Literature 1; Japanese Unexamined Patent Publication JP-A 11-64339

SUMMARY OF INVENTION

Technical Problem

Therefore, the present invention is made in order to solve the above-described problems, and a main object thereof is to reduce the contamination level of an introduction path to a detector, miniaturize a circuit board, and improve measurement accuracy by adjusting the number of molecules of a measurement target component to flow into the detector.

Solution to Problem

That is, a fluid analysis apparatus according to the present invention includes: a detector for measuring concentration of a measurement target component contained in fluid; an introduction path connected to the detector to introduce the fluid into the detector; and a flow rate switching mechanism adapted to, depending on the concentration of the measurement target component, switch a flow rate of the fluid to be introduced into the detector.

The fluid analysis apparatus as described above can produce the following effects because depending on the concentration of the measurement target component, it switches the flow rate of the fluid to be introduced into the detector.

(1) By adjusting the flow rate so as to decrease the number of molecules of the measurement target component contained in the fluid to flow into the detector, the contamination of the introduction path caused by the measurement target component of high concentration can be prevented. By preventing the contamination of the introduction path, an increase in background level can be suppressed.

(2) The number of molecules of the measurement target component to flow into the detector is adjusted, and therefore a detection signal obtained by the detector can be kept within a predetermined range. In doing so, the range of the amplification factor of an amplifier for amplifying the detection signal can be narrowed (preferably, to one), and consequently, a circuit board can be miniaturized.

(3) Since the detection signal obtained by the detector can be kept within the predetermined range, the concentration can be calculated in a range where linearity is ensured, and therefore the measurement can be performed with high accuracy from a low concentration range to a high concentration range. In addition, a concentration measurement range can also be expanded.

(4) Besides, the need for a switching circuit for switching the amplification factor can be eliminated, and therefore the need to take account of noise caused by the switching circuit at the time of switching of the amplification factor can be eliminated. Further, when the fluid analysis apparatus is applied to a vehicle-mounted exhaust gas analysis apparatus, if there is the switching circuit, noise occurs in the switching circuit due to vibration at the time of running; however, in the present invention, the switching circuit is unnecessary, and therefore the need to take account of noise occurring in the switching circuit due to vibration at the time of running can be eliminated.

As a specific embodiment of the introduction path and the flow rate switching mechanism, it is preferable that the introduction path includes a first introduction path and a second introduction path, and the flow rate switching mechanism includes: a first flow rate regulating part provided in the first introduction path to regulate the flow rate of the fluid to a first flow rate; a second flow rate regulating part provided in the second introduction path to regulate the flow rate of the fluid to a second flow rate that is a larger flow rate than the first flow rate; a flow path switching part that switches a flow path to be connected to the detector between the first introduction path and the second introduction path; and a switching control part that compares the concentration obtained by the detector with a predetermined threshold value to control the flow path switching part.

Such a configuration makes it possible to switch between the first flow rate and the second flow rate only by switching a flow path. In addition, by selecting the first flow rate when the measurement target component is of high concentration, or by selecting the second flow rate when the measurement target component is of low concentration, a change in the number of molecules of the measurement target component to flow into the detector can be kept within as narrow a range as possible.

In addition, as another flow rate switching mechanism, it is conceivable to provide, in the introduction path, a device adapted to continuously switch a flow rate, such as a mass flow controller.

Such a configuration makes it possible to keep the change in the number of molecules of the measurement target component to flow into the detector within a further narrower range as compared with the above-described flow path switching case. Note that in terms of the control response speed of a mass flow controller and the simplification of subsequent concentration conversion, the flow path switching configuration as described above is preferable.

In order to miniaturize the circuit board, it is preferable that the fluid analysis apparatus further includes an amplifier that amplifies the detection signal obtained by the detector with a fixed constant amplification factor.

It is preferable that the fluid analysis apparatus further includes a calculation part that calculates the concentration by on the basis of concentration conversion corresponding to the flow rate of the fluid, calculating an output signal resulting from the amplification by the amplifier. Specifically, it is conceivable that the calculation part has concentration conversion expressions respectively corresponding to the flow rates of the fluid, selects a concentration conversion expression on the basis of flow rate data obtained from the flow rate switching mechanism, and calculates the concentration of the measurement target component using the selected concentration conversion expression.

In order to reduce a noise component included in the output signal used for the concentration calculation by the calculation part, it is conceivable to take a moving average of the output signal. Note that at the first flow rate as a lower flow rate, a replacement time (signal rise time) is longer. As a result, there occurs a problem that when taking the moving averages of the output signals at the first and second flow rates using the same averaging time, a response time at the first flow rate becomes longer.

In order to preferably solve this problem to equalize both response times to each other, it is conceivable to making a detection response on the second introduction path side slower than a detection response on the first introduction path side. In particular, it is preferable that the calculation part makes the averaging time for the output signal obtained at the first flow rate shorter than the averaging time for the output signal obtained at the second flow rate.

Also, a fluid analysis method according to the present invention is one using a fluid analysis apparatus including a detector for detecting the concentration of a measurement target component contained in fluid and an introduction path connected to the detector to introduce the fluid into the detector, and depending on the concentration obtained by the detector, switches the flow rate of the fluid to be introduced into the detector.

Advantageous Effects of Invention

According to the present invention configured as described above, since the flow rate of the fluid to be introduced into the detector is switched depending on the concentration obtained by the detector, by adjusting the number of molecules of the measurement target component to flow into the detector, it becomes possible to reduce the contamination level of the introduction path to the detector, miniaturize the circuit board, and improve measurement accuracy.

DESCRIPTION OF EMBODIMENTS

In the following, one embodiment of a fluid analysis apparatus according to the present invention will be described with reference to the drawings.

<Apparatus Configuration>

A fluid analysis apparatus 100 of the present embodiment is an exhaust gas analysis apparatus adapted to measure the concentration of a component contained in exhaust gas discharged from, for example, an internal combustion engine E. Note that the fluid analysis apparatus 100 of the present embodiment is of a direct sampling type that without diluting sampled exhaust gas, directly measures the concentrations.

Figure 1:
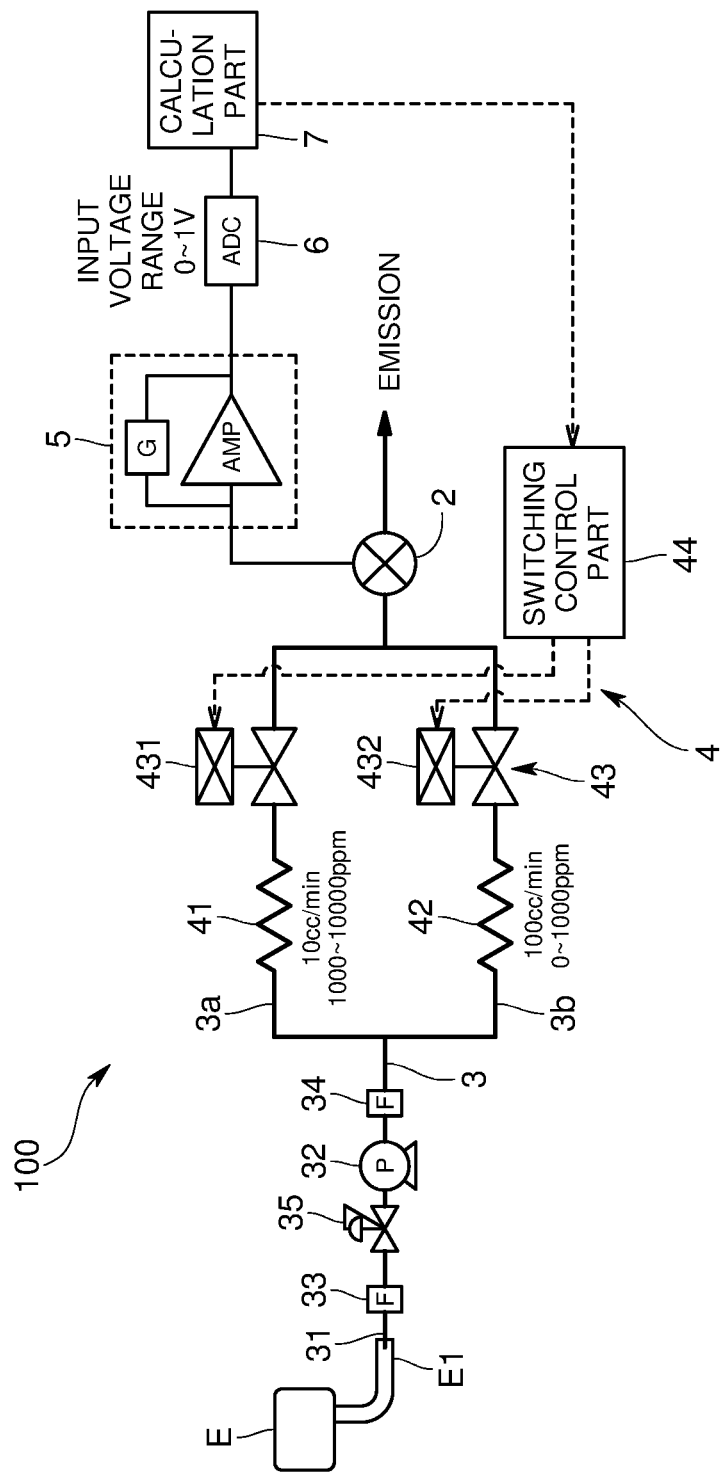
FIG. 1 is a schematic diagram illustrating the configuration of a fluid analysis apparatus according to the present embodiment.

Specifically, as illustrated in FIG. 1, the fluid analysis apparatus 100 includes: a detector 2 for measuring the concentration of a measurement target component contained in the exhaust gas; an introduction path 3 connected to the detector 2 to introduce the exhaust gas into the detector 2; and a flow rate switching mechanism 4 adapted to, depending on the concentration of the measurement target component, switch the flow rate of the exhaust gas to be introduced into the detector 2.

As the detector 2, when the measurement target component contained in the exhaust gas is hydrocarbon (HC), an FID detector adapted to measure the concentration of total hydrocarbons (THC) using a hydrogen flame ionization analysis method (FID) can be used, and when the measurement target component is nitrogen oxide ($NO_x$ ($=NO+NO_2$)), a CLD detector adapted to measure the concentration of nitrogen compounds using a chemiluminescence analysis method (CLD) can be used. In addition, as the detector 2, detectors using various analysis methods respectively suitable for measurement target components can be used, such as a Fourier transform infrared spectrometer (FTIR) and a non-dispersive infrared analyzer (NDIR). Also, as a light source for FTIR or NDIR, a quantum cascade laser (QCL) can be used.

A detection signal (current or voltage signal (analog signal)) obtained by the detector 2 is outputted to an amplifier 5. The amplifier 5 is one that is configured using an operational amplifier and amplifies the detection signal with a fixed constant amplification factor.

Then, an output signal (analog signal) resulting from the amplification by the amplifier 5 is outputted to an A/D converter 6, and converted to a digital signal by the A/D converter 6. The digital signal is outputted to a calculation part 7 and converted into concentration by the calculation part 7.

An introduction path 3 is one of which one end is provided in an exhaust pipe (tail pipe) E1 through which the exhaust gas flows and the other end is connected to the detector 2. Note that "one end of the introduction path 3 is provided in the exhaust pipe E1" means that the one end of the introduction path 3 is provided at a position where the exhaust gas can be sampled, e.g., provided near or inside a discharge port of the exhaust pipe E1.

Specifically, the introduction path 3 includes: a sampling port 31 provided at the one end to sample the exhaust gas; and a suction pump 32 provided downstream of the sampling port 31. In addition, the introduction path 3 is provided with dust filters 33 and 34, a pressure regulation valve 35, and the like. Note that FIG. 1 illustrates the case where the sampling port 31 is provided with the dust filter 33, but not limited to the case.

Also, the introduction path 3 includes a first introduction path 3a and second introduction path 3b that branch on the downstream side of the dust filter 34. The first introduction path 3a and the second introduction path 3b merge on the downstream side, and are connected to the detector 2 downstream of the merging point therebetween.

A flow rate switching mechanism 4 is one adapted to switch the flow rate of the exhaust gas to be introduced into the detector 2 stepwise (in the present embodiment, in two steps).

Specifically, the flow rate switching mechanism 4 includes: a first flow rate regulating part 41 that is provided in the first introduction path 3a to regulate the flow rate of the exhaust gas to a first flow rate $Q_1$; a second flow rate regulating part 42 that is provided in the second introduction path 3b to regulate the flow rate of the exhaust gas to a second flow rate $Q_2$ ($>Q_1$) that is a higher flow rate than the first flow rate $Q_1$; a flow path switching part 43 that switches a flow path to be connected to the detector 2 between the first introduction path 3a and the second introduction path 3b; and a switching control part 44 that compares the concentration of the measurement target component contained in the exhaust gas with a predetermined threshold value to control the flow rate switching part 43. Note that as the concentration of the measurement target component to be compared with the predetermined threshold value by the switching control part 44, not only a concentration value but a concentration-related value is also possible, such as the detection signal (current or voltage signal (analog signal)) from the detector 2, the signal resulting from the amplification by the amplification part 5, or the digital signal from the A/D converter 6.

The first flow rate regulating part 41 and the second flow rate regulating part 42 are configured respectively using constant flow rate devices such as capillary tubes or orifices. In the present embodiment, for example, the first flow rate regulating part 41 is one adapted to regulate the flow rate to a constant flow rate of 10 cc/min, and the second flow rate regulating part 42 is one adapted to regulate the flow rate to a constant flow rate of 100 cc/min.

The flow path switching part 43 includes: a first on-off valve 431 provided downstream of the first flow rate regulating part 41 in the first introduction path 3a; and a second on-off valve 432 provided downstream of the second flow rate regulating part 42 in the second introduction part 3b. The first and second on-off valves 431 and 432 are solenoid valves, and respectively on/off controlled by control signals from the switching control part 44. Note that the flow path switching part 43 may be one adapted to merge the first introduction path 3a and the second introduction path 3b via a three-way solenoid valve, and control the three-way solenoid valve to switch between the flow paths.

The switching control part 44 compares the concentration of the measurement target component obtained by the calculation part 7 and the predetermined threshold value (e.g., 1000 ppm) with each other, and when the concentration is equal to or more than threshold value, opens the first on-off valve 431 and closes the second on-off valve 432 to introduce the exhaust gas into the detector 2 through the first introduction path 3a. On the other hand, when the concentration is less than the threshold value, the switching control part 44 closes the first on-off valve 431 and opens the second on-off valve 432 to introduce the exhaust gas into the detector 2 through the second introduction path 3b. Note that the predetermined threshold value can be arbitrarily determined on the basis of the relationship between the concentration of the measurement target component and the flow rate of the exhaust gas to be introduced into the detector 2 (i.e., the amount of molecules of the measurement target component). For example, by changing the predetermined threshold value to a lower concentration side, resolution on the lower concentration side can be increased to perform the measurement with accuracy. Note that the switching control part 44 may compare the voltage or current signal outputted from the detector 2 or the output signal outputted from the amplifier part 5 with a corresponding threshold value, and on-off control the first and second on-off valves 431 and 432 to switch between the first introduction path 3a and the second introduction path 3b.

Also, in the present embodiment, the voltage signal outputted when the amplification part 5 amplifies the detection signal obtained from the detector 2 when the exhaust gas is introduced into the detector 2 through the first introduction path 3a or the detection signal obtained from the detector 2 when the exhaust gas is introduced into the detector 2 through the second introduction path 3a is set to have 0 to 1 V. That is, the analog signal (the output signal from the amplification part 5) to be inputted to the A/D conversion part 6 is set to have 0 to 1 V.

Further, in the present embodiment, the calculation part 7 calculates the concentration by calculating the digital signal from the A/D conversion part 6 on the basis of concentration conversion corresponding to the flow rate of the exhaust gas. Specifically, the calculation part 7 includes a first concentration conversion expression corresponding to the first flow rate and a second concentration conversion expression corresponding to the second flow rate, and selects a concentration conversion expression on the basis of flow rate data obtained from the switching control part 44 or the like to calculate the concentration of the measurement target component using the selected concentration conversion expression.

Figure 2:
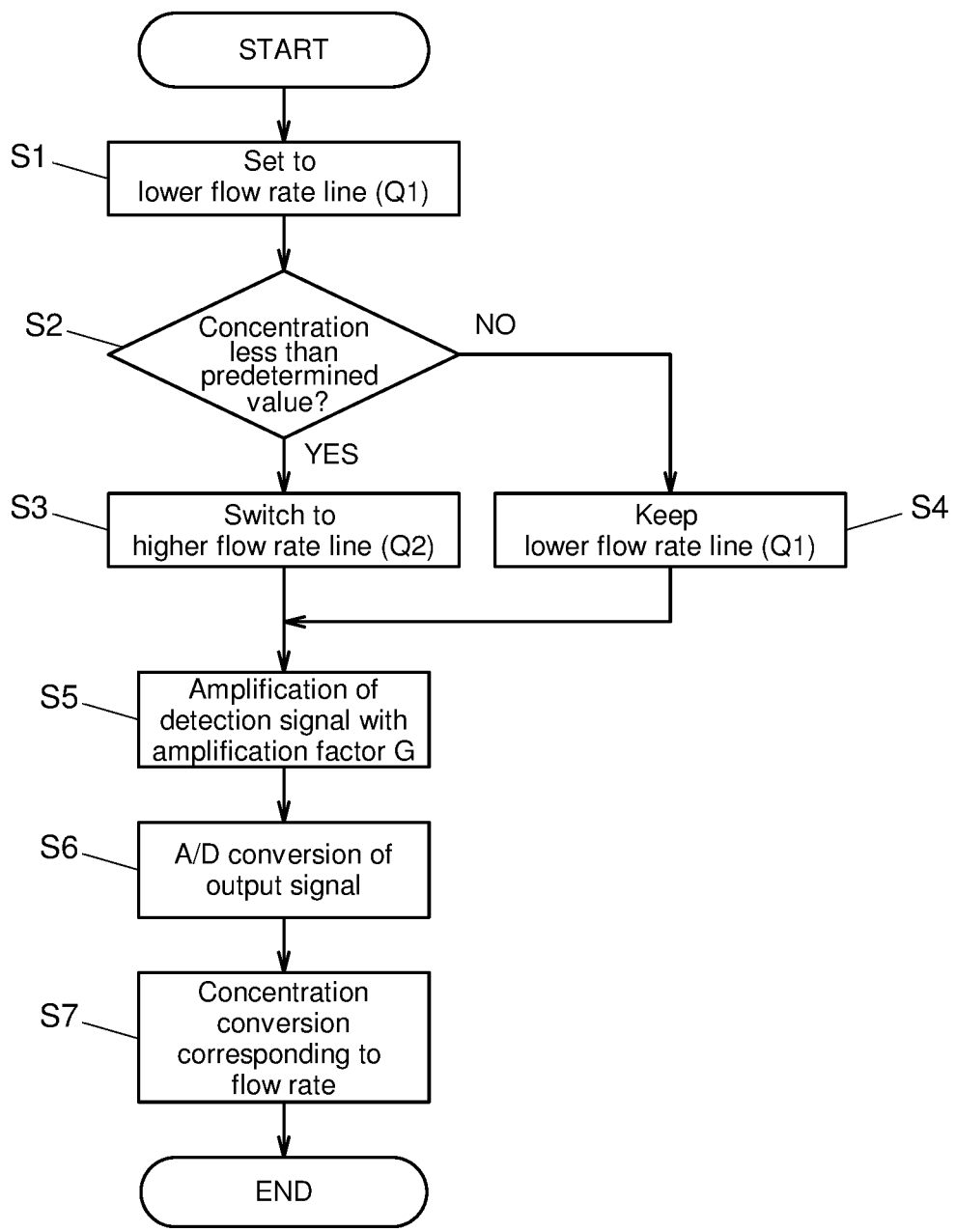
FIG. 2 is a diagram illustrating a flowchart of the operation of the fluid analysis in the same embodiment.

Next, the operation of the fluid analysis apparatus 100 of the present embodiment from the start of the measurement will be described with reference to FIG. 2.

At the start of the exhaust gas analysis, the switching control part 44 opens the first on-off valve 431 and closes the second on-off valve 432 to introduce the exhaust gas (the first flow rate $Q_1$) into the detector 2 through the first introduction path 3a (Step S1). In this state, it is determined whether or not the concentration obtained by the calculation part 7 is less than the predetermined threshold value (Step S2). Then, when the concentration is less than the threshold value, the first on-off valve 431 is closed and the second on-off valve is opened to switch to the second introduction path 3b (the second flow rate $Q_2$) (Step S3). On the other hand, when the concentration is equal to or more than the threshold value, the first on-off valve 431 remains opened and the second on-off valve 432 remains closed to keep the introduction through the first introduction path 3a (Step S4). Note that it may be configured to introduce the exhaust gas into the detector 2 through the second introduction path 3b first, and then switch the flow path in a similar manner to the above.

Subsequently, in either case, the detection signal obtained by the detector 2 is amplified with the constant amplification factor by the amplification part 5 (Step S5), and then the amplified signal is digital converted by the A/D conversion part 6 (Step S6). After that, the calculation part 7 calculates the concentration from the digital signal using a concentration conversion expression corresponding to the flow rate of the exhaust gas flowing into the detector 2 (Step S7).

Note that when, after the start of the analysis, the concentration of the measurement target component varies and thereby a magnitude relationship with the threshold value is changed, the first and second on-off valves 431 and 432 are on-off controlled depending on the magnitude relationship with the threshold value to switch the flow rate of the exhaust gas to flow into the detector 2, and also using a concentration conversion expression corresponding to the resulting flow rate, the concentration is calculated.

<Effects of the Present Embodiment>

The fluid analysis apparatus 100 according to the present embodiment configured as described above can produce the following effects because depending on the concentration obtained by the detector 2 or a concentration-related value related to the concentration, the flow rate of the exhaust gas to be introduced into the detector 2 is switched.

(1) By regulating the flow rate so as to decrease the number of molecules of the measurement target component contained in the exhaust gas to flow into the detector 2, the contamination of the introduction path 3 caused by the measurement target component of high concentration can be prevented. That is, on the higher concentration side, the flow rate of the exhaust gas to flow into the detector 2 is low, and therefore the amount of molecules of the measurement target component can be kept low to thereby prevent the contamination. On the lower concentration side, the flow rate of the exhaust gas to flow into the detector 2 increases; however, the gas of high concentration does not flow, and therefore the amount of molecules of the measurement target component can be kept low to thereby prevent the contamination of the flow path. This also makes it possible to suppress an increase in background level.

(2) Since the number of molecules of the measurement target component to flow into the detector 2 is adjusted, the detection signal obtained by the detector 2 can be kept within a predetermined range. Therefore the number of amplification factors of the amplifier 5 for amplifying the detection signal can be limited to one, and consequently, a circuit board can be miniaturized.

(3) Since the detection signal obtained by the detector 2 can be kept within the predetermined range, the concentration can be calculated in a range where linearity is ensured, and therefore the measurement can be performed with high accuracy from a low concentration range to a high concentration range. In addition, a concentration measurement range can also be expanded.

(4) The need for a switching circuit for switching the amplification factor can be eliminated, and therefore the need to take account of noise caused by the switching circuit at the time of switching can be eliminated.

<Other Embodiments>

Note that the present invention is not limited to the above-described embodiment.

Figure 3:
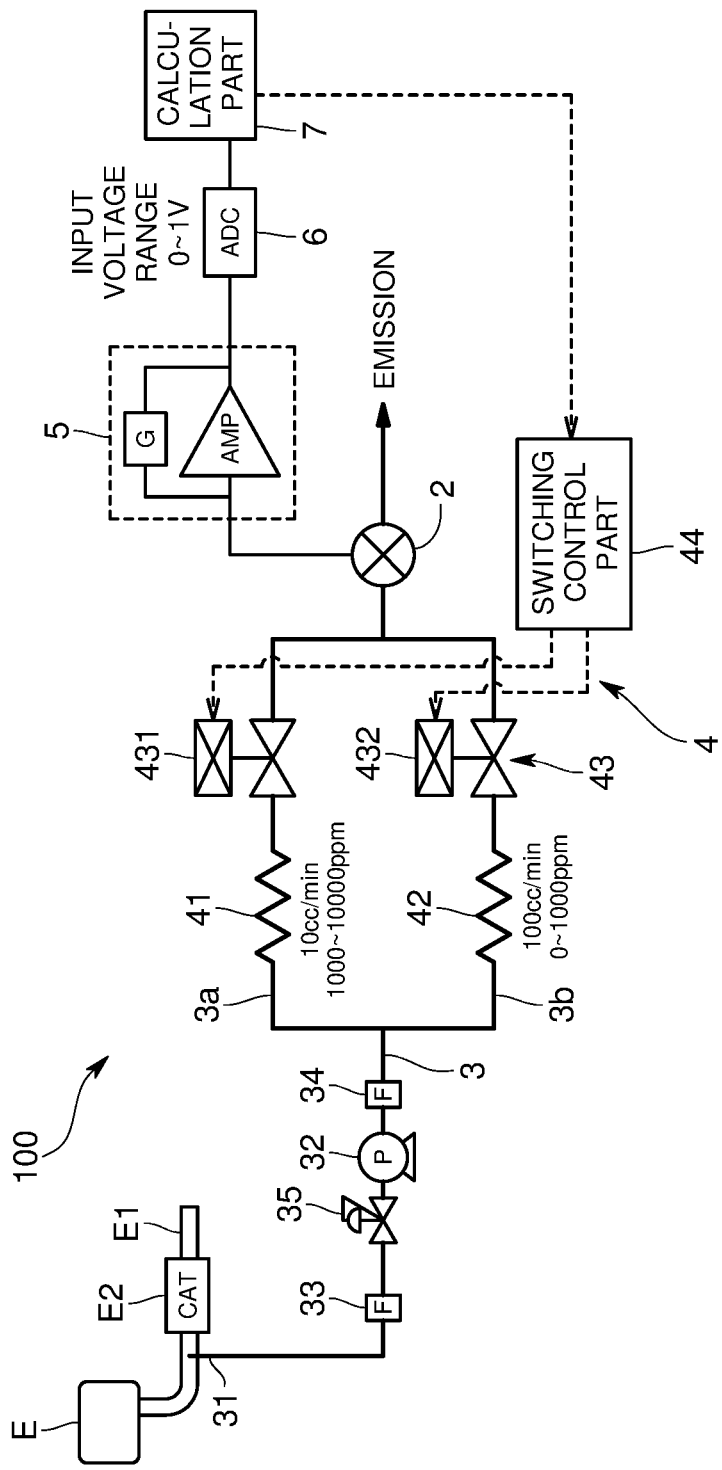
FIG. 3 is a schematic diagram illustrating the configuration of a fluid analysis apparatus according to a variation.

For example, the above-described embodiment is such that the exhaust gas discharged from the exhaust pipe E1 is sampled and analyzed; however, as illustrated in FIG. 3, the present invention may be adapted to connect the one end of the introduction path 3 on the upstream side and/or the downstream side of a catalyst E2 in the exhaust pipe E1, and analyze the exhaust gas before or after passing through the catalyst E2.

The introduction path in the above-described embodiment is one including the first introduction path and the second introduction path, but may be one including three or more introduction paths. In this case, flow rates to be regulated by flow rate regulating parts provided in the respective introduction paths are mutually different, and the flow path switching mechanism switches among the three or more introduction paths.

Also, the calculation part 7 may take the moving average of the digital signal in order to reduce a noise component included in the digital signal used for the concentration calculation. In this case, preferably, the calculation part 7 makes the averaging time for the output signal obtained at the first flow rate shorter than the averaging time for the output signal obtained at the second flow rate. In doing so, the difference between a replacement time (signal rise time) at the first flow rate and a replacement time (signal rise time) at the second flow rate can be cancelled by making the averaging times different, and both response times can be equalized to each other.

Further, in order to equalize the replacement time at the first flow rate and the replacement time at the second flow rate to each other by means of a physical configuration, a dead volume may be formed in the second introduction path 3b using a buffer tank or the like. Alternatively, the second introduction path may be made longer than the first introduction path. Still alternatively, the replacement time at the second flow rate may be equalized to the replacement time at the first flow rate by being added with a predetermined time.

Figure 4:
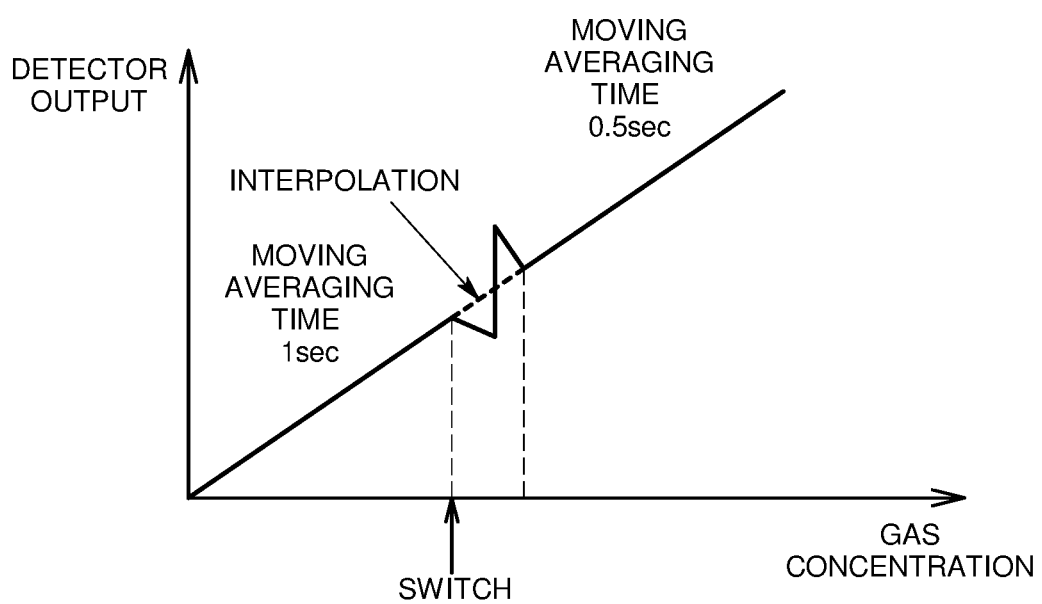
FIG. 4 is a graph illustrating a variation of signal processing by the calculation part.

In addition, as illustrated in FIG. 4, for example, linear interpolation may be applied to the transient response of the detection signal occurring at the time of switching between the first introduction path 3a and the second introduction path 3b using concentrations at stable times before and after the switching.

Also, as the flow rate regulating parts, mass flow controllers may be respectively used. In this case, the number of introduction paths may be one.

Figure 5:
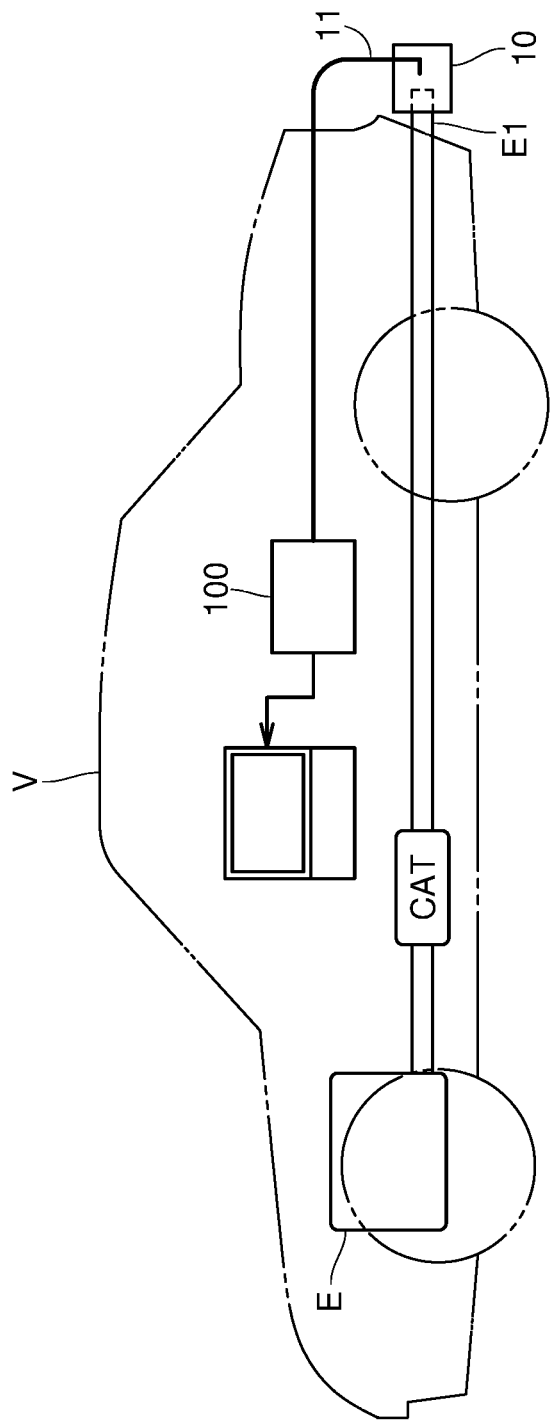
FIG. 5 is a schematic diagram when the fluid analysis apparatus of the present invention is used as a vehicle-mounted type.
Figure 6:
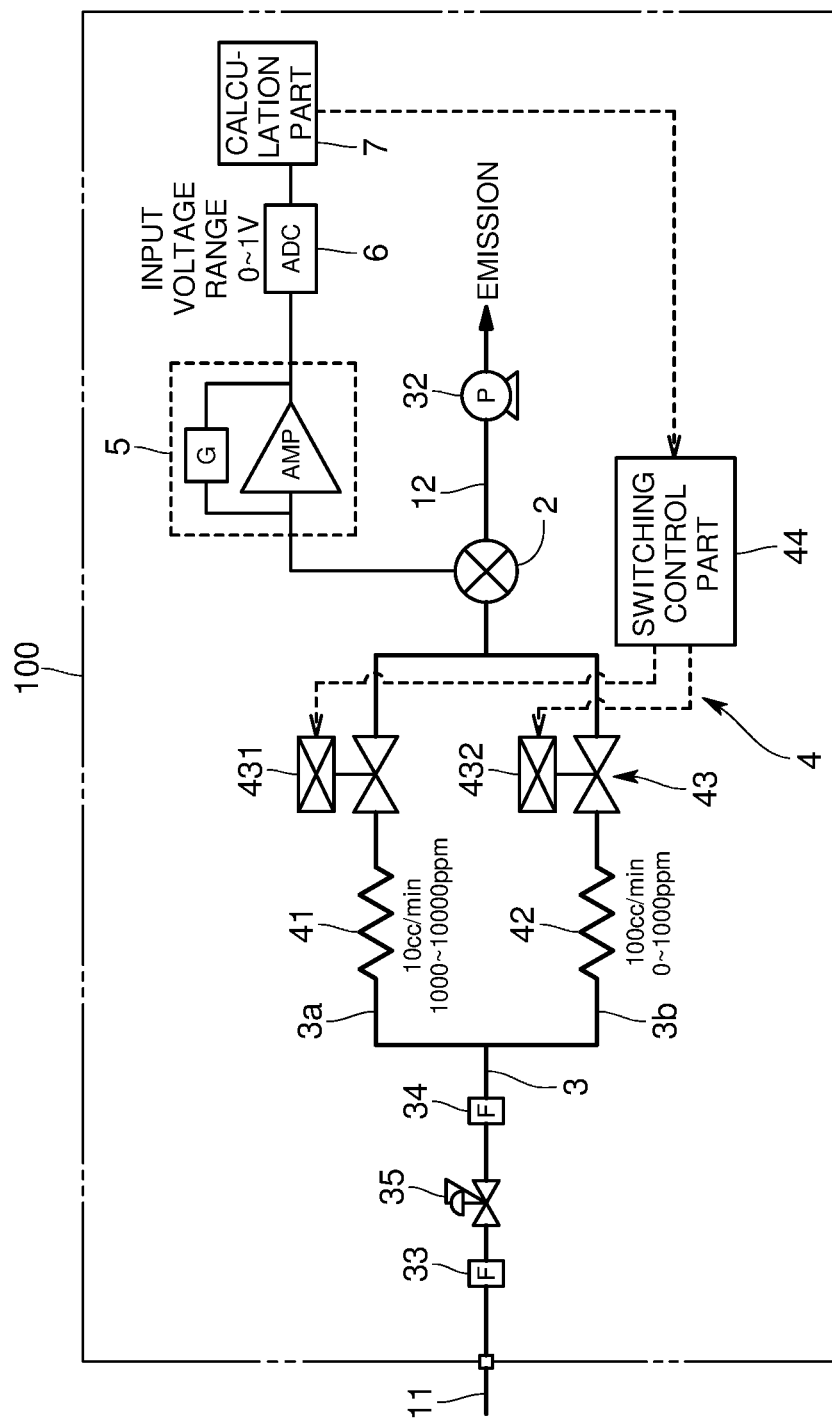
FIG. 6 is a schematic diagram illustrating the configuration of the vehicle-mounted fluid analysis apparatus.

Further, as illustrated in FIG. 5, the fluid analysis apparatus 100 of the present invention may be used as a vehicle-mounted exhaust gas analysis apparatus mounted in, for example, a vehicle V running on an actual road. In this case, exhaust gas to be introduced into the fluid analysis apparatus 100 is sampled through a sampling pipe 11 provided in an attachment pipe (tail pipe attachment) 10 attached to an exhaust pipe (tailpipe) E1. In addition, the sampling pipe 11 is connected to the one end of the introduction path 3. Note that as illustrated in FIG. 6, the suction pump 32 is provided in a downstream side flow path 12 connected on the downstream side of the detector 2, and the detector 2 is used under reduced pressure. Further, as the detector 2 used for the vehicle-mounted exhaust gas analysis apparatus 100, a hydrogen flame ionization analyzer (FID), chemiluminescence analyzer (CLD), Fourier transform infrared spectrometer (FTIR), non-dispersive infrared analyzer (NDIR), or the like can be used. In addition, as a light source for FTIR or NDIR, a quantum cascade laser (QCL) can be used.

When the fluid analysis apparatus 100 is applied to the vehicle-mounted exhaust gas analysis apparatus as described above, if there is a switching circuit for switching the amplification factor, noise occurs in the switching circuit due to vibration at the time of running; however, in the present invention, the switching circuit is unnecessary, and therefore the need to take account of noise occurring in the switching circuit due to vibration at the time of running can be eliminated.

The fluid analysis apparatus of the above-described embodiment is the gas analysis apparatus adapted to analyze a measurement target component contained in gas such as exhaust gas, but may be a liquid analysis apparatus adapted to analyze a measurement target component contained in liquid.

Besides, it should be appreciated that the present invention is not limited to any of the above-described embodiment and variations, but can be variously modified without departing from the scope thereof.

REFERENCE SIGNS LIST

100: Fluid analysis apparatus (gas analysis apparatus)
2: Detector
3: Introduction path
3a: First introduction path
3b: Second introduction path
4: Flow rate switching mechanism
41: First flow rate regulating part
42: Second flow rate regulating part
43: Flow path switching part
44: Switching control part
5: Amplification part
6: A/D conversion part
7: Calculation part

The invention claimed is:

1. A fluid analysis apparatus comprising:
a detector for measuring concentration of a measurement target component contained in fluid;
an introduction path connected to the detector to introduce the fluid into the detector; and
a flow rate switching mechanism provided upstream of the detector in the introduction path, and adapted to compare the concentration obtained by the detector with a predetermined threshold value, and to switch a flow rate of the fluid to be introduced into the detector between (i) a first flow rate when the concentration is equal to or more than the predetermined threshold value, and (ii) a second flow rate that is greater than the first flow rate when the concentration is less than the predetermined threshold value.

2. The fluid analysis apparatus according to claim 1, wherein
the introduction path includes a first introduction path and a second introduction path, and
the flow rate switching mechanism comprises:
a first flow rate regulating part provided in the first introduction path to regulate the flow rate of the fluid to the first flow rate;
a second flow rate regulating part provided in the second introduction path to regulate the flow rate of the fluid to the second flow rate; and
a flow path switching part that switches a flow path to be connected to the detector between the first introduction path and the second introduction path.

3. The fluid analysis apparatus according to claim 2, further comprising
an amplifier that amplifies a detection signal obtained by the detector.

4. The fluid analysis apparatus according to claim 3, further comprising
a calculation part that calculates the concentration by, on a basis of concentration conversion corresponding to the flow rate of the fluid, calculating an output signal resulting from the amplification by the amplifier.

5. The fluid analysis apparatus according to claim 4,
the fluid analysis apparatus making a detection response on a side of the second introduction path slower than a detection response on a side of the first introduction path.

6. The fluid analysis apparatus according to claim 4, wherein
the calculation part is one adapted to perform the concentration conversion by taking a moving average of the output signal and making an averaging time for an output signal obtained at the first flow rate shorter than an averaging time for an output signal obtained at the second flow rate.

7. The fluid analysis apparatus according to claim 1, wherein
the fluid is exhaust gas discharged from an internal combustion engine.

8. The fluid analysis apparatus according to claim 7, wherein
the fluid analysis apparatus is one mounted in a vehicle to analyze the exhaust gas.

9. The fluid analysis apparatus according to claim 1, wherein
the fluid flow rate switching mechanism comprises a device adapted to continuously switch the flow rate in the introduction path.

10. A fluid analysis method using a fluid analysis apparatus comprising a detector for measuring concentration of a measurement target component contained in fluid, an introduction path connected to the detector to introduce the fluid into the detector, and a flow rate switching mechanism provided upstream of the detector in the introduction path, the method comprising:
by the flow rate switching mechanism provided upstream of the detector in the introduction path
comparing the concentration obtained by the detector with a predetermined threshold value, and
switching a flow rate of the fluid to be introduced into the detector between (i) a first flow rate when the concentration is equal to or more than the predetermined threshold value, and (ii) a second flow rate that is greater than the first flow rate when the concentration is less than the predetermined threshold value.

* * * * *